United States Patent [19]

Vinogradoff et al.

[11] Patent Number: 4,992,091

[45] Date of Patent: Feb. 12, 1991

[54] SUBSTITUTED PYRAZOLO[1,5-A]PYRIMIDINE-2-SULFONAMIDES AND COMPOSITIONS AND METHODS OF CONTROLLING UNDESIRED VEGETATION

[75] Inventors: Anna P. Vinogradoff, Concord; William A. Kleschick, Martinez, both of Calif.

[73] Assignee: The Dow Chemical Company, Midland, Mich.

[21] Appl. No.: 884,696

[22] Filed: Jul. 11, 1986

[51] Int. Cl.$^5$ .................. C07D 487/04; A01N 43/54
[52] U.S. Cl. ........................................ 71/92; 544/250; 544/281; 548/375; 548/376; 558/396
[58] Field of Search .................. 544/281, 250, 251; 71/92

[56] References Cited

U.S. PATENT DOCUMENTS 4,349,378  9/1982  Cliff et al. .......................... 71/103
4,650,892  3/1987  Kleschick et al. .................. 544/251
4,740,233  4/1988  Kleschick et al. ...................... 71/92

FOREIGN PATENT DOCUMENTS 244097A  11/1987  European Pat. Off.
0009943  4/1970  Japan ................................. 544/281
951652  3/1964  United Kingdom.

OTHER PUBLICATIONS

Kirkpatrick et al., *J. Med. Chem.*, vol. 20, p. 386 (1977).
Chemical Abstracts, vol. 86 (1977): AN 83509x.
Broadbent et al., *J. Chem. Soc.*, 1965, pp. 3369–3372.

*Primary Examiner*—Donald G. Daus
*Assistant Examiner*—E. Bernhardt
*Attorney, Agent, or Firm*—D. Wendell Osborne; Merlin B. Davey

[57] ABSTRACT

Novel compounds, e.g. 3-cyano-5,7-dimethyl-N-(2,6-dichlorophenyl)pyrazolo]1,5-a]pyrimidine-2-sulfonamide and their use as herbicides and/or for the suppression of nitrification of ammonium nitrogen in soil.

12 Claims, No Drawings

SUBSTITUTED PYRAZOLO[1,5-A]PYRIMIDINE-2-SULFONAMIDES AND COMPOSITIONS AND METHODS OF CONTROLLING UNDESIRED VEGETATION

BACKGROUND OF THE INVENTION

In recent years there has been a great deal of effort directed to the development of sulfonamides having herbicidal activity and several of these compounds have reached the stage of commercialization, i.e., chlorosulfuron and sulfometuron methyl. These compounds exhibit both preemergence and postemergence activity against undesirable vegetation and, in addition, have a low toxicity to animals. The compounds of the prior art may be depicted as follows:

wherein Ar is usually a benzene derivative and Ar' is usually a pyrimidine or symmetrical triazine derivative.

SUMMARY OF THE INVENTION

We have now found that compounds having the formula:

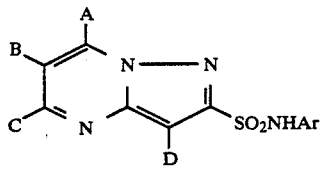

Wherein Ar represents an aromatic (substituted or unsubstituted) or heteroaromatic (substituted or unsubstituted) ring system wherein the substituents are electron withdrawing functional groups in combination with other organic functional groups are exceptionally active herbicides and are readily produced. The aromatic ring may be monocyclic containing six carbon atoms or bicyclic containing ten carbon atoms. The heteroaromatic ring may be monocyclic containing five or six atoms or bicyclic containing nine or ten atoms. The heteroatoms present in the heteroaromatic ring may be a combination of one or more atoms such as nitrogen, oxygen or sulfur.

In addition certain derivatives of compounds of general formula (I) also exhibit herbicidal activity and are effective in beneficially regulating the growth of crops and have the general formulas:

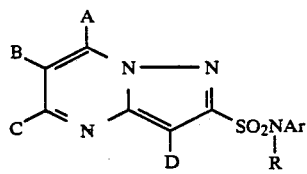

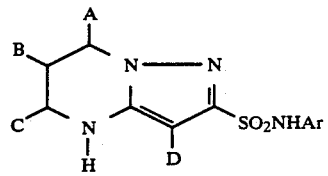

wherein Ar represents an aromatic (substituted or unsubstituted) or heteroaromatic (substituted or unsubstituted) ring system.

DETAILED DESCRIPTION OF THE INVENTION

The aromatic or heteroaromatic ring systems include, for example, phenyl; 1- or 2-napthyl; 2-, 3- or 4-pyridyl; 2- or 3-thienyl; 2- or 3-furyl; 2-, 4- or 5-thiazolyl; 2-, 4- or 5-imidazolyl; 2-, 4- or 5-oxazolyl; 3-, 4- or 5-isothiazolyl; 3-, 4- or 5-isoxazolyl; 3-, 4- or 5-pyrazolyl; 2-benzthiazolyl; 2-benzoxazolyl; 2-benzimidiazolyl and 1-benztriazolyl. Typical examples of substituents found on the aromatic or heteroaromatic ring systems may be one, more than one or a combination of the following: halo (F, Cl, Br, I), $C_1$–$C_4$ alkyl, $C_1$–$C_2$ mono-, di-, tri-, tetra- or perhaloalkyl, phenyl, hydroxy, alkoxy, haloalkoxy, phenoxy, substituted phenoxy, heteroaryloxy, substituted heteroaryloxy, amino, alkylamino, dialkylamino, nitro, alkylthio, haloalkylthio, alkylsulfinyl, haloalkylsulfinyl, alkylsulfonyl, haloalkylsulfonyl, substituted or unsubstituted phenylthio, substituted or unsubstituted phenylsulfinyl, substituted or unsubstituted phenylsulfonyl, cyano, carboxylic acids (and derivatives of carboxylic acids such as esters derived from readily available alcohols and amides derived from ammonia or readily available primary and secondary amines), sulfonic acids (and derivatives of sulfonic acids such as sulfonates derived from readily available alcohols and sulfonamides derived from ammonia or readily available primary or secondary amines), formyl, alkylcarbonyl, haloalkylcarbonyl, phenylcarbonyl, substituted phenylcarbonyl, oximino, oxime ethers, carbinols (and carbinol derivatives such as ethers and esters derived from readily available alkylating agents and carboxylic acids respectively) and mercaptoalkyl (and derivatives of mercaptoalkyl groups such as thioethers and thioesters derived from readily available alkylating agents and carboxylic acids respectively).

The substituents on the pyrazolopyrimidine fragment of structure I are represented by A, B, C and D. Substituents A, B, C and D may be H, alkyl, haloalkyl, hydroxy, alkoxy, haloalkoxy, phenyl, substituted phenyl, halo (F, Cl, Br, I), alkylthio, phenylthio, amino (including alkyl or aryl substituted amino), carboxylic acids and esters. In addition, two adjacent substituents (i.e., A and B or B and C) may be bonded together in a saturated five, six or seven-membered cyclic structure. Examples of such cyclic structures could be represented by A and B or B and C equal to —(CH$_2$)$_n$— where n=3, 4 or 5. These cyclic structures may also contain heteroatoms (e.g., N, O or S) as in the case where A and B or B and C is equal to —(CH$_2$)$_n$O— where n=2 or 3. In the above substituents alkyl, alkenyl, alkynyl and alkoxy in each instance have from 1 to 10 carbon atoms. Substituent D may be H, CO$_2$Et, CN and halo (F, Cl, Br, I).

Preferred compounds of the invention have the general formula:

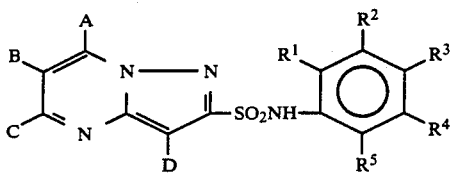

wherein $R^1$ represents halo (F, Cl, Br, I), —$NO_2$, phenyl, —OAr, —$CF_3$, —$OCF_3$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SO_2CF_2CCl_2H$, —$SO_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONHR^8(R^9)$, —$SO_3R^8$ and —$SO_3CH_2CF_3$; $R^2$ and $R^4$ represent H, halo (F, Cl, Br, I), $C_1$-$C_4$ alkyl, $COOR^7$ and —$OR^8$; $R^3$ is H; and $R^5$ represents H, $C_1$-$C_4$ alkyl, $C_1$-$C_4$ alkoxy, halo (F, Cl, Br, I), $NO_2$, $CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONR^8(R^9)$, —$SO_3R^8$, —$SO_3CH_2CF_3$, —$CR^6R^6OR^6$ and —$CR^6R^6SR^6$ and wherein Ar represents substituted or unsubstituted aryl or substituted or unsubstituted heteroaryl, $R^6$ represents H, aryl or $C_1$-$C_4$ alkyl, $R^7$ represents $C_1$-$C_6$ alkyl, alkenyl, alkynyl, aryl, substituted alkyl or substituted aryl and $R^8$ and $R^9$ individually represent $C_1$-$C_4$ alkyl; and A, B and C represent H, $C_1$-$C_4$ alkyl, $C_1$-$C_4$ alkoxy, halo (F, Cl, Br, I), or A and B or B and C can be joined to form a cycloalkyl ring (i.e., —$(CH_2)_n$— wherein n is 3 or 4) or A and B or B and C can be joined to form a ring containing a heteroatom (i.e., —$O(CH_2)_n$— wherein n is 2 or 3); and D represents H, $CO_2Et$, CN and halo (F, Cl, Br, I).

Most preferred compounds of the invention have the general formula:

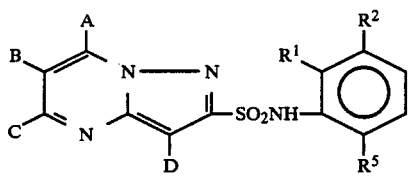

wherein $R^1$ represents $C_1$-$C_4$ alkyl, halo (F, Cl, Br, I), —$NO_2$, —$SR^6$, —$SOR^6$, —$SO_2R^6$, —$COOR^7$ or $CF_3$; $R^2$ represents H, halo (F, Cl, Br, I), $C_1$-$C_4$ alkyl, and $COOR^7$; and $R^5$ represents H, $C_1$-$C_4$ alkyl, $C_1$-$C_4$ alkoxy, halo (F, Cl, Br, I), $CH_2OR^6$, phenyl, $NO_2$ and $COOR^7$ wherein $R^6$ represents $C_1$-$C_4$ alkyl, and $R^7$ represents $C_1$-$C_4$ alkyl, $C_1$-$C_4$ alkenyl, $C_1$-$C_4$ alkynyl, 2-ethoxyethyl and 2-pyridylmethyl and A, B and C independently represent H, halo (F, Cl, Br, I), $C_1$-$C_4$ alkyl or $C_1$-$C_4$ alkoxy, and D independently represents H, CN, $CO_2Et$, and halo (F, Cl, Br, I).

In addition, certain derivatives of compounds corresponding to I also exhibit herbicidal activity and nitrification inhibition activity in soil. Such derivatives include, for example, compounds having the formula:

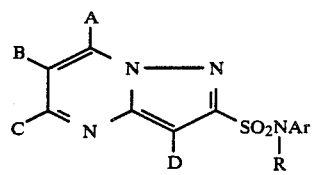

wherein Ar and A, B, C and D are as described above for compound I and R represents alkyl, alkenyl, alkynyl, phenylalkyl, substituted phenylalkyl, acyl, alkoxycarbonyl, phenoxycarbonyl, dialkylaminocarbonyl, alkylsulfonyl, phenylsulfonyl, alkylthiocarbonyl, or phenylthiocarbonyl wherein alkyl, alkenyl and alkynyl are as above defined.

Preferred derivatives of the invention have the general formula:

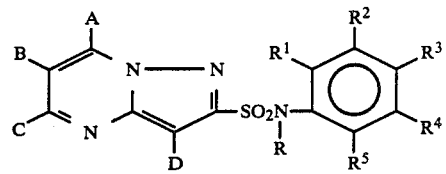

wherein A, B, C, D, $R^1$, $R^2$, $R^3$, $R^4$ and $R^5$ are as described above for I and R represents $C_1$-$C_4$ alkyl, allyl, benzyl, —$COR^{10}$, —$CO_2R^{10}$, —$CONR_2^{10}$, —$COSR^{10}$, and —$SO_2R^{10}$ wherein $R^{10}$ is $C_1$-$C_6$ alkyl, phenyl, substituted phenyl or $C_1$-$C_2$ haloalkyl.

Most preferred derivatives of the invention have the general formula:

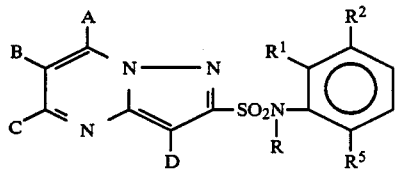

wherein A, B, C, D, $R^1$, $R^2$ and $R^5$ are as described above for I and R is $COR^{10}$ wherein $R^{10}$ is $C_1$-$C_4$ alkyl.

Specifically preferred derivatives of this embodiment of the invention include all of the specifically preferred compounds listed previously in other embodiments of the invention wherein the hydrogen of the sulfonamide portion of their structures ($SO_2NH$) has been replaced with any of the following groups:

1. $COCH_3$.
2. $COCH_2CH_3$.
3. $COCH_2CH_2CH_3$.
4. $COCH(CH_3)_2$.
5. $COCH_2CH_2CH_2CH_3$.
6. $COCH_2CH(CH_3)_2$.
7. $COCH_2C(CH_3)_3$.
8. $COCH_2C_6H_5$.
9. $COcyclo$-$C_6H_{11}$.
10. $COCH=CHC_6H_5$.
11. $COC_6H_5$.
12. $COCH_2Cl$.
13. $COCH_2CH_2Cl$.
14. $COCH_2CH_2COOCH_3$.
15. $COCH_2CH_2COOCH_2CH_3$.
16. $COOCH_3$.
17. $COOCH_2CH_3$.

18. CON(CH₃)₂.
19. C(O)SCH₃.
20. C(O)SCH₂CH₃.
21. SO₂CH₃.
22. SO₂C₆H₅.

Another series of derivatives of compounds of type I also possess herbicidal activity. These compounds are represented by the general formula:

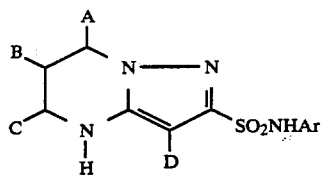
(III)

wherein A, B, C, D and Ar are as described above for compounds of type I.

Preferred compounds of this series of derivatives have the general formula:

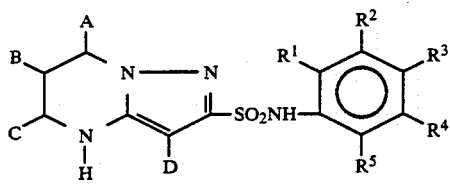

wherein A, B, C, D, R¹, R², R³, R⁴, and R⁵ are as described above for I. Most preferred of these derivatives have the general formula:

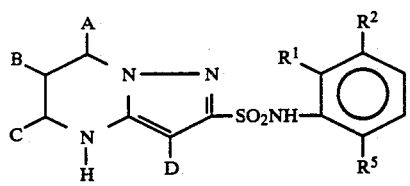

wherein A, B, C, D, R¹, R² and R⁵ are as described above for I.

Furthermore, in the above invention corresponding to general formula III the existence of stereoisomerism is possible. For example stereoisomeric relationships exist when at least one of substituents A, B and C does not equal hydrogen. When only one of substituents A, B and C does not equal hydrogen the compound of type III may exist as a mixture of enantiomers. One enantiomer will be designated as having the R-configuration and the other will be designated as having the S-configuration. Each enantiomer may exhibit different levels of herbicidal activity. When two or more of substituents A, B, or C in structure III do not equal hydrogen, the material may exist as a mixture of diastereomers. For example when two substituents among A, B and C do not equal hydrogen, the compound may exist as two diastereomers. When all three of substituents A, B and C do not equal hydrogen the compound may exist as four diastereomers. In addition all of the diastereomers described above exist as a mixture of two enantiomers. All of the stereoisomers described above, diastereomers and their enantiomeric pairs, may exhibit different levels of herbicidal activity.

The synthesis of compounds of general structure I can be carried out in a straightforward manner as illustrated in Scheme I. Reaction of sulfonyl chloride IV with the appropriate aromatic (substituted or unsubstituted) or heteroaromatic (substituted or unsubstituted) amino compound (ArNH₂) under basic conditions yields the desired product I. The solvent employed is generally pyridine at temperatures ranging from ambient to reflux. Bases which serve as catalysts include pyridine, 4-dimethylaminopyridine and tertiary alkylamines such as triethylamine or N-methylmorpholine. Generally the amino compound serves as the limiting reagent. Molar ratios of between 1.1 and 1.0 for the sulfonyl chloride to amino compound and molar ratios of between 5.0 and 1.1 for the base to amino compound are used most often. A wide range of concentrations may be employed (i.e., 0.1–3M). Generally concentrations in the range of 0.5–2M are used to give homogeneous reaction which proceeds at a convenient rate. The use of pyridine as solvent is convenient as the pyridine can serve both as a solvent and catalyst in the transformation.

SCHEME I

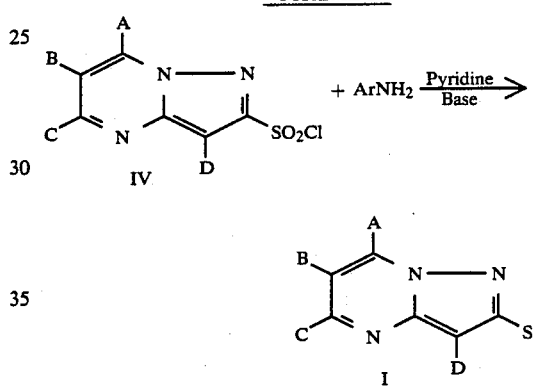

An additional alternative route to compounds of general formula I is illustrated in Scheme II. In cases where the amino compound (ArNH₂) is less reactive (less nucleophilic) it is advantageous to prepare a metal derivative of the amino compound by treatment with a strong base. The corresponding amide bases are generally prepared in ether solvents (i.e., THF) using strong bases such as alkali metal alkyls (i.e., n-BuLi) or alkali metal hydrides (i.e., NaH or KH) at temperatures ranging from −80° C. to 0° C. The amide thus generated in situ can be reacted with sulfonyl chloride IV to yield the desired product I. Generally, molar ratios of the starting amino compound to sulfonyl chloride of 2 to 3 are used to ensure complete reaction.

SCHEME II

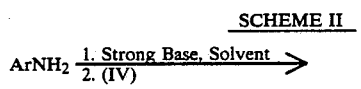

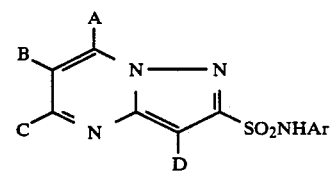

Sulfonyl chlorides IV are new and represent key intermediates in the synthesis of sulfonamides I. Sulfonyl chlorides IV may be prepared according to routes outlined in Scheme III. Benzyl sulfide V may be converted to sulfonyl chloride IV by treatment with $Cl_2$ in an aqueous acid medium. Generally the medium would be aqueous acetic acid or aqueous HCl. The temperature of the reaction mixture is generally maintained between −20° C. and 25° C. during the course of the chlorine addition. Most preferably, temperature ranges between −20° C. and 0° C. are employed to minimize unwanted side reactions such as hydrolysis of IV to the corresponding sulfonic acid. Alternatively, the benzyl sulfide V may be suspended in a two phase system of aqueous acid (i.e., HCl) and an organic solvent (i.e., $CH_2Cl_2$) and treated with sodium hypochlorite. This serves to convert V to the sulfonyl chloride IV in a reproducibly good yield. The solubility of the product in the organic phase serves to protect it from hydrolysis to the sulfonic acid. Again, temperatures in the range of −20° C. to 25° C. are employed with temperatures in the range of −5° C. to 5° C. being most generally used.

SCHEME III

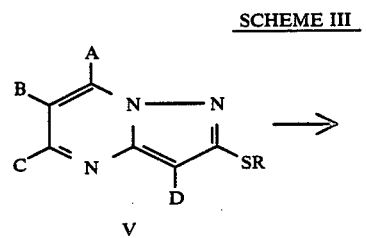

Compounds of general structure V may be prepared by routes illustrated in Scheme IV. Some derivatives analogous to structure V are known materials (i.e., A=C=Me, B=H, D=CN, R=Me) prepared by methods described in *Chem. Ber.*, 95, 2881 (1962). Compound V is prepared directly by reaction of a 1,3-diketone with a 3-amino-5-benzylthiopyrazole VI (R=CH₂Ph) in glacial acetic acid as a solvent. The reaction is performed at temperatures ranging from ambient to reflux. Benzyl sulfide VI can be condensed with not only 1,3-diketones but also beta-keto esters, malonic esters, malonaldehyde, beta-ketoaldehydes or alpha-formyl esters or derivatives thereof (i.e., acetals or enol ethers) to yield products of Type V as illustrated in Table A. Generally these reactions can be carried out under acidic conditions (i.e., glacial acetic acid as a solvent) or basic conditions (i.e., NaOR in ROH wherein R is $C_1$ to $C_4$ alkyl).

SCHEME IV

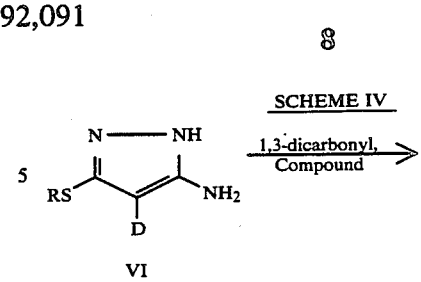

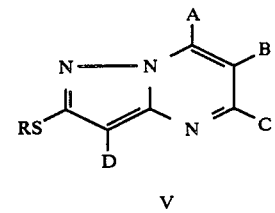

TABLE A

| 1,3-Dicarbonyl Compound or Derivative | Reaction Conditions | Compound of Formula V | | |
|---|---|---|---|---|
| | | A | B | C |
| R−CO−CHR'−CO−R'' | acid | R | R' | R'' |
| R−CO−CHR'−CH(OR)₂ | acid | H | R' | R |
| R−CO−CHR'−CH(OR)₂ | base | R | R' | H |
| R−CO−CHR'−COOR | acid | OH* | R' | R |
| RO−CH(OR)−CHR'−CH(OR)₂ (RO,RO/OR,OR) | acid | H | H | H |
| RO₂C−CHR'−CO₂R | base | OH | R' | OH |

*In this structural representation, as well as others bearing OH groups at 5- or 7-positions of the pyrazolo[1,5-a]pyrimidine, the enol form has been depicted. Clearly this is the equilibrium with the various keto forms.

Compounds of structure VI may be prepared by routes illustrated in Scheme V. Some derivatives analogous to structure VI are known materials (i.e., R=CH₃, D=CN and R=CH₃, D=CO₂Et) prepared by methods described in *Chem. Ber.*, 95, 2881 (1961) and K. Peseke, *Z. Chem.*, 16(1), 16 (1976).

SCHEME V

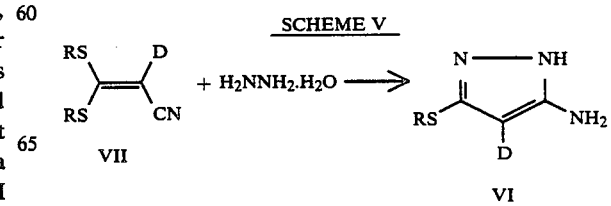

Compounds of general structure VII may be prepared by the route illustrated in Scheme VI. These compounds have been prepared by an alternate method described in *Acta Chem. Scand.*, 22, 1107 (1968).

SCHEME VI

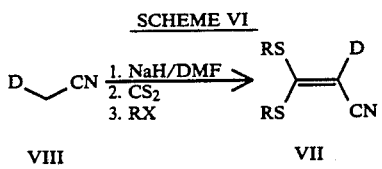

Other compounds of the present invention are best prepared in the manner illustrated in Scheme VII. Compounds such as are represented by I wherein A, B and C are as previously described and D and D' are independently represented by carboalkoxy, nitrile and H can be prepared by this method. The method involves hydrolysis of compound I wherein D is carboalkoxy or nitrile to generate an intermediate compound I wherein D' is a carboxylic acid group which is thermally decarboxylated under the reaction conditions to form I wherein D'=H. Suitable reaction temperatures range from 100° C. to reflux with reaction times of 1 to 7 days.

SCHEME VII

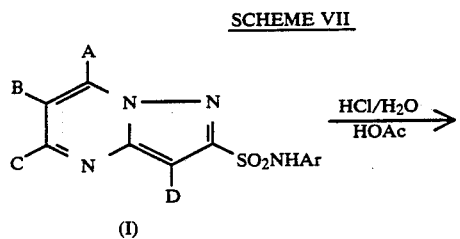

In addition, compounds I of the present invention wherein D=Cl or Br may be prepared by halogenation of the corresponding I wherein D=H. This is illustrated in Scheme VIII wherein compound I where D=H is treated with a halogenating agent to form I wherein D'=Cl or Br. In general, N-halosuccinimide derivatives are the halogenating agents of choice. Reactions are performed in acetonitrile at temperatures ranging from room temperature to 80° C.

SCHEME VIII

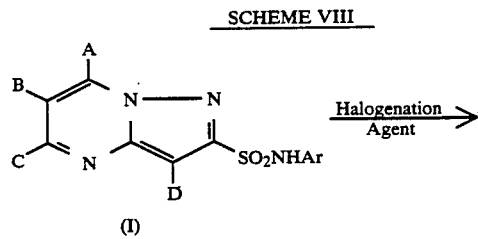

-continued
SCHEME VIII

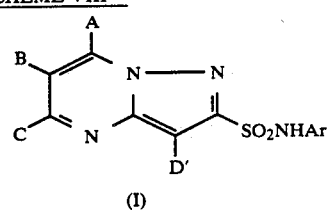

Compounds of the present invention represented by structure II are derived from compounds represented by structure I as illustrated in Scheme IX. The derivatization procedure involves treatment of compound I with a base in a suitable solvent followed by the introduction of an appropriate electrophilic derivatizing reagent. From this process compounds of general structure II can be isolated in good yields. Suitable bases include tertiary alkylamines (i.e., triethylamine), pyridine, 4-dimethylaminopyridine, alkali metal carbonate (i.e., Na$_2$CO$_3$ or K$_2$CO$_3$) and alkali metal alkoxides (i.e., sodium ethoxide or potassium t-butoxide). Suitable solvents include ethers (i.e., tetrahydrofuran), pyridine, acetone, acetonitrile, alcohols (i.e., methanol, ethanol, isopropanol and t-butanol) and polar aprotic solvents (i.e., DMSO and DMF). Suitable electrophilic reagents include alkyl halides, arylalkyl halides (i.e., benzyl chloride), carboxylic acid chlorides, alkyl chloroformates, aryl chloroformates, N,N-dialkyl carbamoyl chlorides, alkyl sulfonyl chlorides, aryl sulfonyl chlorides, alkyl chlorothioformates

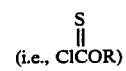

and aryl chlorothioformates

SCHEME IX

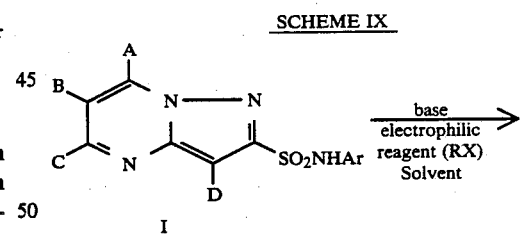

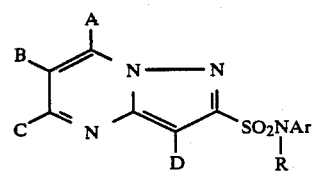

Compounds of the present invention represented by structure III are also derived from compounds represented by structure I as illustrated in Scheme X. The general process involves the reduction of compounds of general structure I with an appropriate reducing agent in a suitable solvent to yield compounds of general structure III. Reducing agents which are effective include metal hydrides (i.e., sodium borohydride) in the presence of acids (i.e., methane sulfonic acid) and hydrogen in the presence of a normal hydrogenation catalyst (i.e., palladium on carbon). For reductions with metal hydrides, polar aprotic solvents (i.e., DMSO) are most frequently used. For reductions using hydrogen and a catalyst, alcohols (i.e., ethanol) are most frequently employed as solvents.

SCHEME X

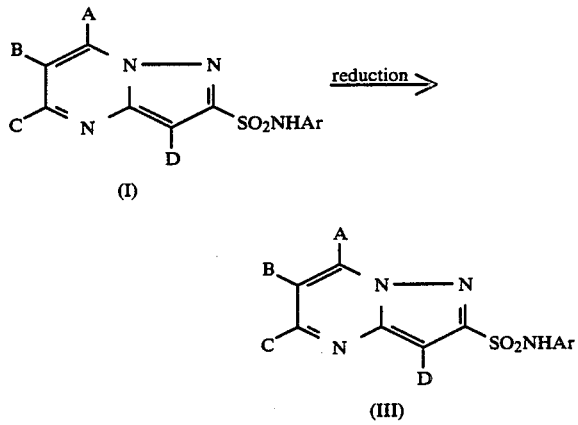

Using the routes illustrated above or minor variations based on the principles illustrated above the novel compounds of this invention can be prepared.

The invention is further illustrated by the following examples. In the following examples NMR data is expressed as delta values downfield from internal tetramethylsilane.

EXAMPLE 1

Preparation of 3,3-bis-benzylthio-2-cyanoacrylonitrile

A slurry of 47.4 g (0.988 mole) of NaH in 300 ml DMF was cooled to 10° C. with stirring under nitrogen. A solution of 32.6 g (0.494 mole) of malononitrile in 50 ml DMF was added to the mixture over 1 hour, keeping the reaction temperature around 10° C. The mixture was allowed to warm to 20° C. then cooled back to 10° C. again and a solution of 37.7 g (0.495 mole) of carbon disulfide in 70 ml DMF was added over 1.5 hours. The mixture was warmed to 20° C. and stirred for 1 hour, then cooled to 10° C. and a solution of 125 g (0.988 mole) of benzyl chloride in 100 ml DMF was added over 45 minutes. The mixture was stirred cold for 30 minutes, then allowed to warm to ambient, and heated at 80° C. for 20 hours. The mixture was then cooled and thrown onto 3 l ice/water and the whole was transferred to a separatory funnel. Upon addition of Et$_2$O, a solid formed in the separatory funnel. This was collected by filtration, dried briefly on a porous plate and recrystallized from 2-propanol to give 70 g (44 percent) of tan crystals, m.p. 70°–80° C. A further recrystallization from 2-propanol gave 56.3 g (35.3 percent) of pale tan crystals, m.p. 80° C. (lit m.p. 83°–84° C., K. A. Jensen & L. Henriksen, Acta Chem. Scand., 22, 1107 (1968)). $^1$H NMR (DMSO-d-6): 7.4 (s, 10H, aromatic), 4.5 (s, 4H, —CH$_2$—). $^{13}$C NMR (DMSO-d-6): 180.6, 134.9, 129.1, 128.8, 128.1, 112.8, 79.1. IR (KBr): 2210, 1490, 1450 cm$^{-1}$. Analysis: Calculated for C$_{18}$H$_{14}$N$_2$S$_2$: C, 67.24; H, 4.38; N, 8.69. Found: C, 66.81; H, 4.45; N, 8.65.

EXAMPLE 2

Preparation of ethyl 3,3-bis-benzylthio-2-cyanoacrylate

A slurry of 81.6 g (1.70 mole) of NaH in 750 ml DMF was stirred under nitrogen at 10° C. To this slurry was added a solution of 95.7 g (0.85 mole) of ethyl cyanoacetate in 150 ml DMF dropwise over 1 hour 40 minutes, keeping the temperature at or around 10° C. The cooling bath was removed for 10 minutes, then the mixture was cooled to 0° C. and 64.6 g (0.85 mole) of carbon disulfide in 120 ml DMF was added dropwise over 3.5 hours, keeping the temperature at or below 10° C. The mixture was then allowed to warm to ambient and stirred for 16 hours. The mixture was again cooled with an ice bath as a solution of 176.8 g (1.69 mole) of benzyl chloride in 225 ml DMF was added dropwise to the reaction mixture, keeping the temperature around 20°–25° C. The mixture was heated at 70° C. for 1 hour, then stirred for 16 hours at ambient. The mixture was thrown onto ice-water and stirred vigorously as a yellow precipitate formed. The precipitate was collected by filtration and stood on a porous plate for 3 hours. Recrystallization from a minimum (1.8 l) of hot absolute EtOH gave 217.3 g (69.5 percent) of off-white rhomboids, m.p. 81.5°–83.5° C. An additional 8.0 g (2.6 percent) of off-white crystals were obtained from the mother liquor, m.p. 81°–82.5° C. Total yield 72.1% (lit m.p. 85°–86° C., K. Jensen & L. Henriksen, Acta Chem. Scand., 22, 1107 (1968)). $^1$H NMR (DMSO-d-6): 7.34–7.27 (m, 10H, aromatic), 4.45 (s, 2H, —CH$_2$S—), 4.33 (s, 2H, —CH$_2$S—), 4.16 (q, 2H, —OCH$_2$—), 1.20 (t, 3H, CH$_3$). $^{13}$C NMR (DMSO-d-6): 175.4, 161.2, 135.5, 135.0, 129.1, 128.7, 128.6, 127.9, 127.7, 115.8, 101.8, 61.6, 41.3, 13.9. IR (KBr): 2200, 1670, 1435, 1240, 1155, 1130, 1010 cm$^{-1}$. Analysis: Calculated for C$_{20}$H$_{19}$NO$_2$S$_2$: C, 65.31; H, 5.25; N, 3.68. Found: C, 65.01; H, 5.18; N, 3.79.

EXAMPLE 3

Preparation of 3-amino-5-benzylthio-4-cyanopyrazole.

A slurry of 16.4 g (51 mmole) of 3,3-bis-benzylthio-2-cyanoacrylonitrile in 50 ml 2-propanol was stirred at room temperature as a solution of 2.6 g (51.4 mmole) hydrazine monohydrate in 20 ml 2-propanol was added over 15 minutes, and the mixture became a homogeneous solution. The mixture was stirred for 1 hour, then 100 ml water was added, and a solid gradually separated from the medium. This solid was collected by filtration and washed with 2-propanol. The bulk of the filtrate was added to ice and the resultant solid collected by filtration. The solids were combined and washed with 2-propanol, then triturated with 1:1 2-propanol/Et$_2$O and collected by filtration. The solid was washed with 1:1 2-propanol/Et$_2$O, then Et$_2$O before drying, and gave 7.87 g (67.5 percent) of the product as a white powder, m.p. 151°–153° C. $^1$H NMR (DMSO-d-6): 12.0 (br. s, 1H, NH), 7.3 (m, 5H, aromatic), 6.5 (br. s, 2H, NH$_2$), 4.2 (s, 2H, —CH$_2$—). $^{13}$C NMR (DMSO-d-6): 154, 145, 137, 128, 127, 74, 35. IR (KBr): 3420, 3200, 2200, 1635, 1590, 1510, 1370, 1335 cm$^{-1}$. Analysis: Calculated for C$_{11}$H$_{10}$N$_4$S: C, 57.37; H, 4.38; N, 24.33. Found: C, 57.08; H, 4.46; N, 24.46.

EXAMPLE 4

Preparation of 3-amino-5-benzylthio-4-carboethoxypyrazole

A solution of 185.0 g (0.501 mole) of ethyl 3,3-bis-benzylthio-2-cyanoacrylate in 200 ml THF/500 ml EtOH/100 ml CH$_3$OH was stirred at room temperature as a solution of 25.1 g (0.500 mole) of hydrazine hydrate in 225 ml EtOH was added dropwise. The mixture was stirred at room temperature for 16 hours. As the mixture was concentrated in vacuo, a white precipitate formed. This was collected by filtration, washed with 2-propanol and dried to give 114.5 g (82.6 percent) of the product as a white powder, m.p. 125°–126.5° C. $^1$H NMR (DMSO-d-6): 11.9 (br. s, 1H, NH), 7.5–7.2 (m, 5H, benzene), 6.1 (br. s, 2H, NH$_2$), 4.2 (s, 2H, CH$_2$S), 4.1 (q, 2H, CH$_2$O), 1.2 (t, 3H, CH$_3$). $^{13}$C NMR (DMSO-d-6): 163.2, 152.6, 146.4, 138.2, 128.9, 128.2, 126.8, 91.3, 58.6, 33.6, 14.4. IR (KBr): 3500, 3400–3200, 3000–2900, 1640, 1560, 1530, cm$^{-1}$. Analysis: Calculated for C$_{13}$H$_{15}$N$_3$O$_2$S: C, 56.30; H, 5.45; N, 15.15. Found: C, 56.35; H, 5.36; N, 15.31.

EXAMPLE 5

Preparation of 2-benzylthio-3-cyano-5,7-dimethlpyrazolo[1,5-a]pyrimidine

A slurry of 0.5 g (2.2 mmole) of 3-amino-5-benzylthio-4-cyanopyrazole in 15 ml glacial HOAc was stirred at room temperature as 0.44 g (4.4 mmole) of 2,4-pentanedione was added. The mixture was stirred at room temperature for 3 hours. The white solid was collected by filtration, washed with HOAc, and dried to give 0.62 g (95.4 percent) of product as a white powder, m.p. 140° C. The analytical sample was recrystallized from 2-propanol. $^1$H NMR (DMSO-d-6): 7.5 (m, 2H, benzene), 7.3 (m, 3H, benzene), 7.1 (s, 1H, pyrazolopyrimidinyl H-6), 4.5 (s, 2H, CH ), 2.7 (s, 3H, CH ), 2.5 (s obscured by DMSO, 3H, CH$_3$). $^{13}$C NMR (DMSO-d-6): 163.3, 155.3, 150.5, 146.7, 137.0, 129.1, 128.3, 127.3 112.8, 111.1, 79.0, 34.5, 24.1, 16.3. IR (KBr): 2220, 1615, 1550 cm$^{-1}$. Analysis: Calculated for C$_{16}$H$_{14}$N$_4$S: C, 65.28; H, 4.79; N, 19.03; S, 10.89. Found: C, 65.11; H, 4.64; N, 18.95; S, 11.03.

EXAMPLE 6

Preparation of 2-benzylthio-3-carboethoxy-5,7-dimethylpyrazole

A slurry of 95.1 g (0.343 mole) 3-amino-5-benzylthio-4-carboethoxypyrazole in 350 ml glacial HOAc was stirred at room temperature as a solution of 68.7 g (0.686 mole) of 2,4-pentanedione in 181 ml glacial HOAc was added dropwise over 1.5 hours. The mixture was stirred at room temperature for 18 hours. The solid was collected by filtration, washed with glacial HOAc and dried to give 104.5 g (89.2 percent) of product as a white powder, m.p. 159°–160° C. A further 9.5 g (8.1 percent) of product was obtained by adding the filtrate to ice and collecting the white precipitate, m.p. 157°–159° C. $^1$H NMR (DMSO-d-6): 7.7–7.3 (m, 5H, aromatic), 7.18 (s, 1H, H-6), 4.5 (s, 2H, CH$_2$S), 4.32 (q, 2H, OCH$_2$), 2.76 (s, 3H, CH$_3$), 2.59 (s, 3H, CH$_3$), 1.30 (t, 3H, CH$_3$). IR (KBr): 1670, 1610, 1550, 1490, 1470, 1440, 1375, 1350, 1300, 1235, 1205, 1160, 1145, 1050 cm$^{-1}$. Analysis: Calculated for C$_{18}$H$_{19}$N$_3$O$_2$S: C, 63.32; H, 5.61; N, 12.31. Found: C, 63.32; H, 5.59; N, 12.39.

EXAMPLE 7

Preparation of 3-cyano-5,7-dimethylpyrazolo-[1,5-apyrimidine-2-sulfonyl chloride A solution of 4.7 g (16 mmole) 2-benzylthio-3-cyano-5,7-dimethylpyrazolo[1,5-a]pyrimidine in 80 ml CH$_2$Cl$_2$ was stirred with 63 ml water containing 4.1 ml concentrated HCl (49.2 mmole) and cooled with an ice-water bath. To this cold solution was added 69 ml 5 percent aqueous NaOCl (48.3 mmole) dropwise over 25 minutes. At end of addition, the mixture was stirred cold for 45 minutes, then the organic layer was separated and washed sequentially with dilute NaHSO$_3$, H$_2$O and brine, then dried over Na$_2$SO$_4$. After filtration and evaporation of solvent in vacuo, a golden oil was obtained. This oil was diluted with 1-2 ml EtOAc, and hexane added till a solid separated. This solid was collected by filtration, washed with minimal EtOAc/hexane and vacuum-dried briefly at room temperature. This gave 3.0 g (70 percent) of crude product as a yellow solid. An analytical sample was carefully recrystallized from 2-propanol, m.p. 138° C. $^1$H NMR (DMSO-d-6): 7.1 (s, 1H, H-6), 2.7 (s, 3H, CH$_3$), 21.5 (s, 3H, CH$_3$). $^{13}$C NMR (DMSO-d-6): 163.5, 162.0, 150.0, 147.3, 113.0, 111.9, 78.0, 24.2, 16.3. IR (KBr): 2250, 1630, 1550, 1440, 1400, 1170 cm$^{-1}$. Analysis: Calculated for C$_9$H$_7$N$_4$O$_2$SCl: C, 39.93; H, 2.61; N, 20.70. Found: C, 40.07, H, 2.66; N, 20.83.

EXAMPLE 8

Preparation of 3-carboethoxy-5,7-dimethylpyrazolo-[1,5-a]pyrimidine-2-sulfonyl chloride A solution of 4.0 g (11.7 mmole) 3-benzylthio-4-carboethoxy-5,7-dimethylpyrazolo1,5-a]pyrimidine in 68 ml CH$_2$Cl$_2$ was stirred at 0° C. with 46 ml H$_2$O and 2.9 ml conc. HCl as 51 ml (35.7 mmole) aqueous 5 percent NaOCl was added over 55 minutes. The mixture was stirred cold for an additional 30 minutes, then the organic layer was separated and washed sequentially with dilute NaHSO$_3$, H$_2$O and brine, then dried over Na$_2$SO$_4$. After filtration and evaporation of solvent, a yellow residue was obtained. This was triturated with hexane and collected by filtration and gave, after drying, 3.09 g (83 percent) crude product as an off-white solid, m.p. 128°–130° C. $^1$H NMR (CDCl$_3$): 7.0 (s, 1H, H-6), 4.23 (q, 2H, CH$_2$O), 2.41 (s, 3H, CH$_3$), 2.35 (s, 3H, CH$_3$), 1.4 (t, 3H, CH$_3$). $^{13}$C NMR (CDCl$_3$): 165.4, 159.9, 155.1, 148.4, 146.9, 128.4, 127.4, 113.5, 100.8, 61.7, 25.5, 16.8, 13.9. IR (KBr): 3000–2800, 1700, 1630, 1545, 1470, 1440, 1380, 1240, 1180. Analysis: Calculated for C$_{11}$H$_{12}$N$_3$O$_4$SCl: C, 41.58; H, 3.81; N, 13.23. Found: C, 41.18; H, 3.81; N, 13.10.

EXAMPLE 9

Preparation of 3-cyano-5,7-dimethyl-N-(2,6-dichlorophenyl)-pyrazolo[1,5-a]pyrimidine-2-sulfonamide A solution of 0.67 g (4.1 mmole) of 2,6-dichloroaniline was stirred at room temperature as a solution of 1.1 g (4.1 mmole) of 3-cyano-5,7-dimethylpyrazolo[1,5-a]pyrimidine-2-sulfonyl chloride in 3 ml pyridine was added. The mixture was heated at 70° C. for 15 hours, then at 130° C. for 24 hours, and cooled to room temperature. The mixture was diluted with 2-propanol and stirred at room temperature for 1 hour. The tan solid was collected by filtration, washed well with 2-propanol and dried to give 0.9 g tan powder. This was completely dissolved in 2N NaOH and extracted with $CH_2Cl_2$. The aqueous layer was separated and acidified with glacial HOAc, which gave a precipitate. This was collected by filtration, washed well with water and dried to give 0.2 g (12.3 percent) of the product as an off-white solid, m.p. 280°–285° C. (decomposition and degassing). $^1H$ NMR (DMSO-d-6): 11.1 (br., 1H, NH), 7.5–7.4 (m, 3H, benzene), 7.5 (s, 1H, pyrazolopyrimidinyl H-6), 2.67 (s, 3H, $CH_3$), 2.63 (s, 3H, $CH_3$). $^{13}C$ NMR (DMSO-d-6): 165, 156, 150, 148, 136, 130, 129, 114, 111, 80, 24, 16. IR (KBr): 3220, 2240, 1620, 1540, 1440, 1355, 1170 $cm^{-1}$. Analysis: Calculated for $C_{15}H_{11}N_5O_2SCl_2$: C, 45.46; H, 2.80; N, 17.68. Found: C, 45.56; H, 2.82; N, 17.84.

EXAMPLE 10

Preparation of
3-carboethoxy-5,7-dimethyl-N-(2,6-dichlorophenyl)-pyrazolo-[1,5-a]pyrimidine-2-sulfonamide A solution of 1.53 g (9.4 mmole) 2,6-dichloroaniline was stirred in 10 ml pyridine at room temperature as 3.0 g (9.4 mmole) of 4-carboethoxy-5,7-dimethyl-pyrazolo1,5-a]pyrimidine-2-sulfonylchloride was added as a solid. The mixture was stirred at room temperature for 1.5 hours, heated at 135° C. for 4 hours, at 120° C. for 16 hours and then cooled to room temperature. Most of the pyridine was evaporated in vacuo to give a dark brown residue. This was taken up in minimal HOAc and thrown onto ice. The $HOAc-H_2O$ mother liquor was decanted, leaving an oily brown residue. This was stirred with acetone and filtered to give 0.23 g of a dark brown solid wet cake. The filtrate contained a brown oily residue, which was combined with the brown solid wet cake and the whole was stirred with dilute NaOH and $CH_2Cl_2$. Both layers were extremely dark. The aqueous base fraction was separated, and Celite was added to it. It was then filtered and the filtrate was acidified with dilute HCl which gave a tan solid. This solid was collected by filtration, washed well with water and stood upon a porous plate, during which it hardened to a dark brown glassy solid. This was vacuum-oven dried and gave 0.36 g (8.6 percent) of product, m.p. 207° C. $^1H$ NMR (DMSO-d-6): 9.90 (s, 1H, NH), 7.50–7.25 (m, 4H, benzene and pyrazolopyrimidinyl H-6), 4.23 (q, 2H, $OCH_2$), 2.66 (s, 3H, $CH_3$), 2.60 (s, 3H, $CH_3$), 1.23 (t, 3H, $CH_3$). IR (KBr): 3600–2800, 1670, 1620, 1540, 1470, 1450, 1390, 1350, 1240, 1220, 1180, 1170, 1140, 1050 $cm^{-1}$). M/e: 442.0292. Analysis: Calculated for $C_{17}H_{16}N_4O_4SCl_2$: C, 46.06; H, 3.64; N, 12.64. Found: C, 46.02; H, 3.60; N, 12.80.

EXAMPLE 11

Preparation of
3-cyano-5,7-dimethyl-N-(2,6-difluorophenyl)-pyrazolo[1,5-a]pyrimidine-2-sulfonamide A solution of 0.7 g (5.3 mmole) of 2,6-difluoroaniline and 0.9 g (7.4 mmole) 4-dimethylaminopyridine in 10 ml pyridine was stirred at room temperature as 1.44 g (5.3 mmole) 3-cyano-5,7-dimethylpyrazolo[1,5-a]pyrimidine-2-sulfonyl chloride was added as a solid. The mixture exothermed slightly during addition. The mixture was heated at 60°–65° C. for 2 hours, then at room temperature for 16 hours. Acetone was added to the mixture, which gave a precipitate. Solids were removed by filtration, and the filtrate was concentrated in vacuo to give a dark brown viscous residue. This was dissolved in $CH_2Cl_2$ and stirred with dilute NaOH at room temperature. The aqueous phase was separated and the procedure repeated. The combined aqueous phases were stirred with ice and acidified with dilute HCl till no further precipitate formed. The precipitate was collected by filtration, washed with water and dried to give 0.86 g (44.8 percent) of the product as a tan powder, m.p. 244° C. (dec.). $^1H$ NMR (DMSO-d-6): 10.9 (br., 1H, NH), 7.42 (m, 2H) and 7.18 (m, 2H) (benzene and pyrazolopyrimidinyl H-6), 2.65 (s, 3H, $CH_3$), 2.62 (s, 3H, $CH_3$). IR (KBr): 3230, 2240, 1620, 1600, 1550, 1475, 1435, 1410, 1360, 1290, 1240, 1220, 1200, 1170, 1010. Analysis: Calculated for $C_{15}H_{11}N_5O_2SF_2$: C, 49.58; H, 3.05; N, 19.28. Found: C, 49.18; H, 3.15; N, 18.89.

EXAMPLE 12

Preparation of
5,7-dimethyl-N-(2,6-difluorophenyl)pyrazolo[1,5-a]pyrimidine-2-sulfonamide A slurry of 4.8 g (10.8 mmole) of 3-carboethoxy-5,7-dimethyl-N-(2,6-difluorophenyl)pyrazolo[1,5-a]pyrimidine-2-sulfonamide in 30 ml glacial HOAc was stirred at room temperature with 1 ml concentrated HCl and 3 ml water for 2 hours. The mixture was then heated at 110° C. for 16 hours. A further 1 ml concentrated HCl and 5 ml water were added and the mixture stirred for 16 hours, then cooled to room temperature. The mixture was thrown onto ice and the resultant solid collected by filtration, washed with water and dried to give 2.34 g (64 percent) of the product as a brown powder, m.p. 201°–208° C. An analytical sample was recrystallized from $CH_3CN/EtOAc/CH_3OH$, m.p. 209°–211° C. (dec). $^1H$ NMR (DMSO-d-6): 10.3 (s, 1H, NH), 7.37 (m, 1H, benzene), 7.10 (m including s, 3H, aromatic and H-3 or H-6), 6.82 (s, 1H, H-3 or H-6), 2.63 (s, 3H, $CH_3$), 2.53 (s, 3H, $CH_3$). IR (KBr): 3400, 3050, 2800, 1625, 1600, 1540, 1480, 1430, 1325, 1290, 1240, 1170, 1140, 1000. Analysis: Calculated for $C_{14}H_{12}N_4F_2O_2S$: C, 49.70; H, 3.58; N, 16.56. Found: C, 48.68; H, 3.74, N, 15.98.

EXAMPLE 13

Preparation of
3-carboethoxy-5,7-dimethyl-N-(2,6-difluorophenyl)-pyrazolo[1,5-a]pyrimidine-2-sulfonamide A solution of 4.04 g (31.3 mmole) of 2,6-difluoroaniline in 20 ml pyridine with 3.82 g (31.3 mmole) of 4-dimethylaminopyridine was stirred at room temperature as 9.9 g (31.3 mmole) of 3-carboethoxy-5,7-dimethylpyrazolo[1,5-a]pyrimidine-2-sulfonyl chloride was added as a solid in portions, the last portion being washed in with 5 ml pyridine. The mixture initially exothermed slightly. The mixture was stirred for 16 hours at room temperature, then at 120° C. for 2 hours, then cooled to room temperature. The mixture was diluted with acetone and the solids collected by filtration and discarded. The filtrate was concentrated in vacuo to give a brown residue which was dissolved in $CH_2Cl_2$ and extracted 2×with 25 ml 2N NaOH. The basic fractions were combined, filtered and acidified with concentrated HOAc. A tan precipitate formed and was collected by filtration, washed well with water, then stood on a porous plate prior to vacuum-oven drying, and gave 1.55 g (12.1 percent) of product as a tan powder with dark glassy portions. M.p. behavior:

the tan powder darkens to a glass at 58° C., which then melts at 148°-160° C. When the glass is formed separately and cooled, the material then melts at 88°-110° C. $^1$H NMR (DMSO-d-6): 9.9 (br., 1H, NH), 7.34 (m, 1H, aromatic), 7.25 (s, 1H, H-6), 7.10 (m, 2H, aromatic), 4.24 (q, 2H, OCH$_2$), 2.66 (s, 3H, CH$_3$), 2.58 (s, 3H, CH$_3$), 1.23 (t, 3H, CH$_3$). IR (KBr): 3300-2900, 1680, 1625, 1600, 1545, 1480, 1440-1410, 1360, 1325, 1300, 1240, 1170. Analysis: Calculated for C$_{17}$H$_{16}$N$_4$F$_2$O$_4$S: C, 49.75; H, 3.93; N, 13.65. Found: C, 49.95; H, 3.93; N, 13.56.

EXAMPLE 14

Preparation of 3-chloro-5,7-dimethyl-N-(2,6-difluorophenyl)-pyrazolo[1,5-a]pyrimidine-2-sulfonamide A slurry of 1.56 g (4.6 mmole) of 5,7-dimethyl-N-(2,6-difluorophenyl)pyrazolo[1,5-a]pyrimidine-2-sulfonamide in 12 ml CH$_3$CN was stirred at room temperature as a solution of 0.62 g (4.6 mmole) N-chlorosuccinimide in 12 ml CH$_3$CN was added. After stirring at room temperature for 4 hours, the reaction mixture was added to ice and stirred, then stood at room temperature. A tan precipitate was collected by filtration, washed well with water, then dried to give 1.23 g (71.9 percent) of product as a brown powder, m.p. 194.5°-196° C. $^1$H NMR (DMSO-d-6): 10.6 (br., 1H, NH), 7.4 (m, 1H, aromatic), 7.20 (s, 1H, H-6), 7.10 (m, 2H, aromatic), 2.60 (s, 3H, CH$_3$), 2.45 (s, 3H, CH$_3$). IR (KBr): 3200-2600, 1620, 1540, 1500, 1480, 1425, 1335, 1290, 1240, 1185, 1170, 1010, 790. Analysis: Calculated for C$_{14}$H$_{11}$N$_4$C, 45.10; H, 2.97; N, 15.03. Found: C, 44.83; H, 3.03; N, 14.48.

EXAMPLE 15

Preparation of 3-carboethoxy-5,7-dimethyl-N-(2-trifluoromethyl-6-methoxyphenyl)pyrazolo-[1,5-a]pyrimidine-2-sulfonamide A solution of 1.79 g (9.4 mmole) of 2-trifluoromethyl-6-methoxyaniline in 2 ml pyridine was stirred at room temperature as 2.98 g (9.4 mmole) of 3-carboethoxy-5,7-dimethylpyrazolo[1,5-a]pyrimidine--2sulfonyl chloride was added in portions as a solid. The mixture was stirred at room temperature for 16 hours. The mixture was diluted with acetone, which gave a fine almost white precipitate. This was collected by filtration and dried to give 1.20 g (27 percent) of product as an off-white powder, m.p. 231°-233° C. (dec). The filtrate was concentrated in vacuo and gave a brown flake-like residue. This was dissolved in CH$_2$Cl$_2$ and extracted with dilute NaOH. The base fraction was separated and acidified with glacial HOAc. A precipitate formed and was collected by filtration, washed with water, and dried to give 0.75 g (16.9 percent) of product as a tan powder, m.p. 227°-229° C. (dec). $^1$H NMR (DMSO-d-6): 9.15 (s, 1H, NH), 7.42 (m, 1H, aromatic), 7.15 (m, 3H, aromatic and H-6), 4.35 (q, 2H, OCH ), 3.18 (s, 3H, OCH$_3$), 2.70 (s, 3H, CH$_3$), 2.60 (s, 3H, CH$_3$), 1.30 (t, 3H, CH3). IR (KBr): 3600-2700, 1680, 1625, 1545, 1485, 1440, 1400, 1325, 1280, 1240, 1210, 1200, 1170, 1147, 1120, 1090, 1045 cm$^{-1}$. Analysis: Calculated for C$_{119}$H$_{19}$N$_4$F$_3$O$_5$S: C, 48.30; H, 4.05; N, 11.86; S, 6.79. Found: C, 48.02; H, 4.05; N, 11.90; S, 6.86.

EXAMPLE 16

Preparation of 5,7-dimethyl-N-(2-trifluoromethyl-6-methoxyphenyl)-pyrazolo-[1,5-a]pyrimidine-2-sulfonamide A slurry of 1.2 g (2.5 mmole) 3-carboethoxy-5,7-dimethyl-N-(2-trifluoromethyl-6-methoxyphenyl)-pyrazolo[1,5-a]pyrimidine-2-sulfonamide in 10 ml glacial HOAc was stirred at room temperature as 4 ml 6N HCl was added. The mixture was heated at 105° C. for 4 hours, then at reflux for 16 hours, then cooled to room temperature. The mixture was thrown onto ice and a solid separated. This was collected by filtration, washed well with water and dried to give 0.81 g (81 percent) of product as an off-white powder, m.p. 258°-262° C. (dec). $^1$H NMR (DMSO-d-6): 9.95 (s, 1H, NH), 7.48 (m, 1H, aromatic), 7.26 (m, 2H, aromatic), 7.09 (s, 1H, H-3 or H-6), 6.81 (s, 1H, H-3 or H-6), 3.14 (s, 3H, OCH$_3$), 2.70 (s, 3H, CH$_3$), 2.54 (s, 3H, CH$_3$). IR (KBr): 3050, 2840, 2670, 1630, 1550, 1480, 1445, 1355, 1325, 1275, 1170, 1145, 1100, 1045 cm$^{-1}$.

Analysis: Calculated for C$_{16}$H$_{15}$N$_4$F$_3$O$_3$S: C, 48.00; H, 3.78; N, 13.99. Found: C, 47.37; H, 3.69; N, 13.70.

EXAMPLE 17

Preparation of 3-chloro-5,7-dimethyl-N-(2-trifluoromethyl-6-methoxyphenyl)-pyrazolo[1,5-a]pyrimidine-2-sulfonamide A slurry of 0.5 g (1.2 mmole) 5,7-dimethyl-N-2-trifluoromethyl-6-methoxyphenyl)pyrazolo[1,5-a]-pyrimidine-2-sulfonamide in 3 ml CH$_3$CN was stirred with a solution of 0.17 g (1.2 mmole) of N-chlorosuccinimide in 3 ml CH$_3$CN for 16 hours at room temperature. A further 2 ml CH$_3$CN was added and the mixture was heated at 75° C. for 8 hours, then cooled and stirred at room temperature for 16 hours. The mixture was heated at 85° C. for 2 hours, then 0.04 g (0.3 mmole) N-chlorosuccinimide was added and the mixture was heated an additional 2 hours. The mixture was cooled to room temperature and added to ice, which gave a tan precipitate. The precipitate was collected by filtration, washed well with water, and dried to give 0.36 g (69 percent) of product as a tan powder, m.p. 198° C. (dec). $^1$H NMR (DMSO-d-6): 10.1 (br. s, 1H, NH), 7.49 (m, 1H, aromatic), 7.27 (m, 2H, aromatic), 7.18 (s, 1H, H-6), 3.32 (s, 3H, OCH3), 2.58 (s, 3H, CH3), 2.49 (s, 3H, CH3) IR (KBr): 3100, 1620, 1540, 1520, 1480, 1430, 1350, 1325, 1160, 1110, 1050 cm$^{-1}$. Analysis: Calculated for C$_{16}$H$_{14}$N$_4$ClF$_3$O$_3$S: C, 44.19; H, 3.25; N, 12.89. Found: C, 44.14; H, 3.28; N, 12.90.

The compounds prepared employing the above general procedures and the appropriate starting materials are tabulated in the following Tables I-V.

TABLE I

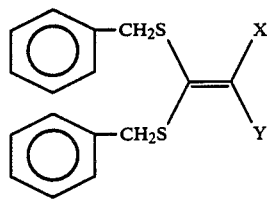

| Compound | X | Y | M.P. °C. | Elemental Analysis | C | H | N |
|---|---|---|---|---|---|---|---|
| 1 | CN | CN | 80 | Calc. for $C_{18}H_{14}N_2S_2$: | 67.24 | 4.38 | 8.69 |
|   |    |    |    | Found: | 66.81 | 4.45 | 8.65 |
| 2 | CN | $CO_2Et$ | 81.5–83.5 | Calc. for $C_{20}H_{19}NO_2S_2$: | 65.31 | 5.25 | 3.68 |
|   |    |    |    | Found: | 65.01 | 5.18 | 3.79 |

TABLE II

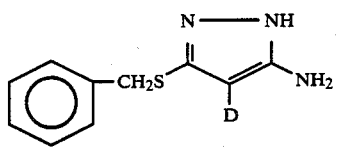

| Compound | D | Melting Point | Elemental Analysis | C | H | N |
|---|---|---|---|---|---|---|
| 3 | CN | 151–153° C. | Calc. for $C_{11}H_{10}N_4S$: | 57.37 | 4.38 | 24.33 |
|   |    |    | Found: | 57.08 | 4.46 | 24.46 |
| 4 | $CO_2Et$ | 125–126.5° C. | Calc. for $C_{13}H_{15}NO_3S$: | 56.30 | 5.45 | 15.15 |
|   |    |    | Found: | 56.35 | 5.36 | 15.31 |

TABLE III

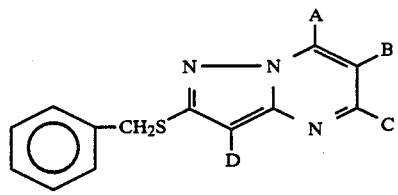

| Compound | D | A | B | C | Melting Point | Elemental Analysis | C | H | N |
|---|---|---|---|---|---|---|---|---|---|
| 5 | CN | Me | H | Me | 140° C. | Calc. for $C_{16}H_{14}N_4S$: | 65.28 | 4.79 | 19.03 |
|   |    |    |   |    |    | Found: | 65.11 | 4.64 | 18.95 |
| 6 | $CO_2Et$ | Me | H | Me | 157–159° C. | Calc. for $C_{18}H_{19}N_3O_2S$: | 63.32 | 5.61 | 12.31 |
|   |    |    |   |    |    | Found: | 63.32 | 5.59 | 12.39 |

TABLE IV

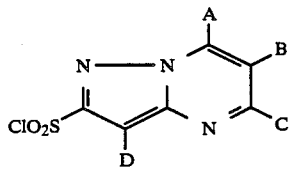

| Compound | D | A | B | C | Melting Point | Elemental Analysis | C | H | N |
|---|---|---|---|---|---|---|---|---|---|
| 7 | CN | Me | H | Me | 138° C. | Calc. for $C_9H_7N_4ClO_2S$: | 39.93 | 2.61 | 20.70 |
|   |    |    |   |    |    | Found: | 40.07 | 2.66 | 20.83 |
| 8 | $CO_2Et$ | Me | H | Me | 132–134° C. | Calc. for $C_{11}H_{12}N_3O_4SCl$: | 41.58 | 3.81 | 13.23 |
|   |    |    |   |    |    | Found: | 41.18 | 3.81 | 13.10 |

TABLE V

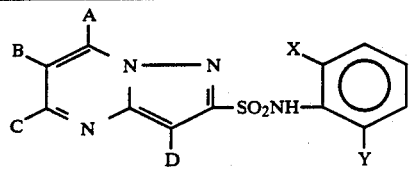

| Compd. | X | Y | D | A | B | C | Melt. Pt. (°C.) | Elemental Analysis | C | H | N |
|---|---|---|---|---|---|---|---|---|---|---|---|
| 9 | Cl | Cl | CN | Me | H | Me | 280–285(d) | Calc. for $C_{15}H_{11}N_5O_2SCl_2$: | 45.46 | 2.80 | 17.68 |
|   |    |    |    |    |   |    |            | Found:                                | 45.56 | 2.82 | 17.84 |
| 10 | Cl | Cl | $CO_2Et$ | Me | H | Me | 207° | Calc. for $C_{17}H_{16}N_4O_4SCl_2$: | 46.06 | 3.64 | 12.64 |
|    |    |    |          |    |   |    |      | Found:                                | 46.02 | 3.60 | 12.80 |
| 11 | F | F | CN | Me | H | Me | 244(d) | Calc. for $C_{15}H_{11}N_5O_2SF_2$: | 49.58 | 3.05 | 19.28 |
|    |   |   |    |    |   |    |        | Found:                               | 49.18 | 3.15 | 18.89 |
| 12 | F | F | H | Me | H | Me | 209–211(d) | Calc. for $C_{14}H_{12}N_4F_2O_2S$: | 49.70 | 3.58 | 16.56 |
|    |   |   |   |    |   |    |            | Found:                               | 48.68 | 3.74 | 15.98 |
| 13 | F | F | $CO_2Et$ | Me | H | Me | 148–160 | Calc for $C_{17}H_{16}N_4F_2O_4S$: | 49.75 | 3.93 | 13.65 |
|    |   |   |          |    |   |    |         | Found:                              | 49.95 | 3.93 | 13.56 |
| 14 | F | F | Cl | Me | H | Me | 194.5–196 | Calc. for $C_{14}H_{11}N_4ClF_2O_2S$: | 45.10 | 2.97 | 15.03 |
|    |   |   |    |    |   |    |           | Found:                                 | 44.83 | 3.03 | 14.48 |
| 15 | $CF_3$ | $OCH_3$ | $CO_2Et$ | Me | H | Me | 227–229(d) | Calc. for $C_{19}H_{19}N_4F_3O_5S$: | 48.30 | 4.05 | 11.86 |
|    |        |         |          |    |   |    |            | Found:                               | 48.02 | 4.05 | 11.90 |
| 16 | $CF_3$ | $OCH_3$ | H | Me | H | Me | 258–262(d) | Calc. for $C_{16}H_{15}N_4F_3O_3S$: | 48.00 | 3.78 | 13.99 |
|    |        |         |   |    |   |    |            | Found:                               | 47.37 | 3.69 | 13.70 |
| 17 | $CF_3$ | $OCH_3$ | Cl | Me | H | Me | 198(d) | Calc. for $C_{16}H_{14}N_4ClF_3O_3S$: | 44.19 | 3.25 | 12.89 |
|    |        |         |    |    |   |    |        | Found:                                 | 44.14 | 3.28 | 12.90 |

The compounds of the present invention are highly effective herbicides when applied to the locus of vegetation, herein defined as encompassing preemergent (soil) applications as well as postemergent (foliar) applications. They have utility for broadspectrum pre- and/or postemergence weed control in areas where complete vegetation control is desired. The subject compounds are also useful for selective pre- and/or postemergence weed control in crops such as wheat. Certain of these compounds are effective for the control of nutsedge (Cyperus spp.) and some compounds may be used for selective weed control in corn, soybeans and rice.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat ® 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic ® 61 (molecular weight about 1000), polyethylene glycol ester of tall oil acids, sodium octophenoxyethoxyethyl sulfate, tris(polyoxyethylene)sorbitan monostearate (Tween ® 60), and sodium dihexylsulfosuccinate.

The herbicidally effective concentration of the active ingredients in solid or liquid compositions generally is from about 0.00003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulators, pesticides and the like and can be formulated with solid particulate fertilizer carriers such as ammonium nitrate, urea and the like.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application. In such embodiments, the pesticidal compound is employed as a supplemental toxicant for the same or for a different pesticidal use or as an additament.

The compounds of the present invention are particularly useful in combination with other herbicides including the substituted urea herbicides such as 3-(3,4-dichlorophenyl)-1,1-dimethylurea, 3-(3,4-dichlorophenyl)-1-methoxy-1-methylurea (Lorox ®) and 1,1-dimethyl-3-($\alpha,\alpha,\alpha$-trifluoro-m-tolyl)urea (Cotoran ®); the triazines such as 2-chloro-4-(ethylamino)-6-(isopropylamino)-s-triazine and 2-chloro-4-(1-cyano-1-methylethylamino)-6-ethylamino-s-triazine (Bladex ®); the uracils such as 5-bromo-3-sec-butyl-6-methyluracil; N-(phosphonomethyl)glycine; the phenoxys such as 2,4-dichlorophenoxyacetic acid; picolinic acids such as 4-amino-3,5,6-trichloropicolinic acid (Tordon ®) and 3,6-dichloropicolinic acid (Lontrel ®); 4-chloro-2-butynyl-3-chlorophenyl carbamate (Carbyne ®); diisopropylthiocarbamic acid, ester with 2,3-dichloroallyl alcohol (Avadex ®); diisopropylthiocarbamic acid, ester with 2,3,3-trichloroallyl alcohol (Avadex ® BVD); ethyl-N-benzoyl-N-(3,4-dichlorophenyl)-2-aminopropionate (Suffix ®); 1,2-dimethyl-3,5-diphenylpyrazolium methylsulfate (Avenge ®); methyl (2-[4-(2,4-dichlorophenoxy)phenoxy]propanoate) (Hoelon ®); butyl 2-[4-(5-(trifluoromethyl)-2-pyridinyl)oxy]phenoxy]propanoate (Fusilade ®); esters of 2-[4-(3-chloro-5-trifluoromethyl)-2-pyridinyl)oxy]phenoxy]propionic acid; 4-amino-6-tert-butyl-3-(methylthio)-1,2,4-triazin-5-(4H)-one (Lexone ®); 3-isopropyl-1H-2,1,3-benzothiadiazin-(4)-3H-one 2,2-dioxide; $\alpha,\alpha,\alpha$-trifluoro-2,6-dinitro-N,N-dipropyl-p-toluidine; 1,1'-dimethyl-4,4'-bipyridinium ion; 2-chloro-2',6'-diethyl-(methoxymethyl)acetanilide; and 2-1-(ethoxyimino)-butyl]-5-(2-ethylthio)propyl]-3-hydroxy-2-cyclohexen-1-one (Poast ®).

The rates of application for compounds of the invention are determined by a number of factors including the active ingredient being applied, the particular action desired (e.g., general or selective control), the plant species to be modified and the stage of growth thereof, the part of the plant to be contacted with the toxic active ingredient, the formulation selected, weather and climate, etc. Thus, it is to be understood that all of the active ingredients of the present invention and compositions containing the same may not be equally effective at similar concentrations or against the same plant species. In non-selective preemergence and foliar treatments, the active ingredients of the invention are usually applied at an approximate rate of from about 0.01 to about 10 pounds/acre. In pre- and postemergence operations for selective uses, a dosage of about 0.01 to about 10 pounds/acre is generally applicable, a rate of 0.01 to 4 pounds/acre being preferred.

The following example illustrates the effect of the compounds of this invention applied postemergently.

Plant species in this and other tests were the following:

| Common Name | Scientific Name |
|---|---|
| A. cotton | Gossypium spp. |
| B. rape | Brassica napus |
| C. soybean | Glycine max. |
| D. sugar beet | Beta saccharifera |
| E. cocklebur | Xanthium spp. |
| F. jimsonweed | Datura stramonium |
| G. annual morning glory | Ipomoea spp. |
| H. pigweed | Amaranthus spp. |
| I. velvetleaf | Abutilon theophrasti |
| J. corn | Zea mays |
| K. rice | Oryza sativa |
| L. sorghum | Sorghum vulgare |
| M. wheat | Triticum aestivum |
| N. barnyardgrass (watergrass) | Echinochloa crusgalli |
| O. crabgrass | Digitaria spp. |
| P. yellow foxtail | Setaria lutescens |
| Q. johnson grass | Sorghum halepense |
| R. wild oats | Avena fatua |
| S. sprangletop | Leptochloa filiformis |
| T. yellow nutsedge | Cyperus esculentus |

EXAMPLE 18

In representative operations, each compound to be utilized in a series of tests is dissolved in acetone to one-half of the final volume (twice the final concentration) to be used and the acetone solution in each case is admixed with an equal volume of water containing 0.1 percent by weight of surface active material. The compositions, generally in the nature of an emulsion, were employed to spray separate respective plant species which had been grown to a 2–4 leaf stage in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other plants were left untreated to serve as controls. After treatment, the plants were maintained for about two weeks under greenhouse conditions conducive for good plant growth and watered as necessary. The specific plant species, test compound and dosage and the percent postemergent control obtained are set forth in the table below. Control refers to the reduction in growth compared to the observed results of the same untreated species.

that all sulfur containing substituents are in the same oxidation state.

2. Compound of claim 1 which is 3-cyano-5,7-dimethyl-N-(2,6-dichlorophenyl)pyrazolo[1,5-a]pyrimidine-2-sulfonamide.

3. Compound of claim 1 which is 3-carboethoxy-5,7-dimethyl-N-(2,6-dichlorophenyl)pyrazolo[1,5-a]pyrimidine-2-sulfonamide.

| Compound | Dosage (ppm) | POSTEMERGENT CONTROL OF PLANT SPECIES Plant Species | | | | | | | | | | | | | | | | |
|---|---|---|---|---|---|---|---|---|---|---|---|---|---|---|---|---|---|---|
| | | A | B | C | D | E | F | G | H | I | J | K | L | M | N | O | P | Q | R | T |
| 9 | 2000 | 30 | 70 | 40 | 60 | 50 | NT | 0 | 100 | 75 | 0 | 0 | 0 | 0 | 20 | 100 | 100 | 50 | 40 | 70 |
| 10 | 2000 | 90 | 80 | 75 | 80 | — | 100 | — | 0 | 30 | 50 | 25 | 0 | 0 | 30 | 60 | — | 60 | 0 | 80 |
| 11 | 2000 | 60 | 100 | 80 | 30 | 40 | 20 | 70 | — | 75 | 20 | 20 | 0 | 0 | 20 | 0 | 80 | 35 | 0 | 0 |
| 12 | 1000 | 0 | — | 0 | 0 | 0 | 0 | 0 | 100 | 20 | 0 | 30 | 0 | 0 | 0 | 0 | 0 | 0 | 0 | 0 |
| 13 | 1000 | 50 | — | 90 | 40 | — | — | 70 | 100 | 60 | 0 | 0 | 0 | 0 | 0 | 40 | 50 | 40 | 0 | 0 |
| 14 | 62.5 | 100 | 100 | 80 | 70 | — | 70 | 80 | 100 | 80 | 60 | 0 | 20 | 20 | 30 | 70 | 80 | 0 | 35 | 0 |
| 15 | 1000 | 0 | 40 | 70 | 40 | — | 80 | 80 | 30 | 20 | 54 | 0 | 30 | 20 | 40 | 80 | 80 | 0 | 30 | 0 |
| 16 | 1000 | 0 | 40 | 20 | 40 | — | 80 | 80 | 0 | 30 | 40 | 20 | 0 | 0 | 75 | 80 | 80 | 80 | 40 | 0 |
| 17 | 1000 | 98 | 98 | 98 | 80 | — | 80 | 80 | 100 | 98 | 80 | 80 | 80 | 45 | 80 | 95 | 98 | 90 | 80 | 80 |

| Compound | Dosage (lb./acre) | PREEMERGENT CONTROL OF PLANT SPECIES Plant Species | | | | | | | | | | | | | | | | |
|---|---|---|---|---|---|---|---|---|---|---|---|---|---|---|---|---|---|---|
| | | A | B | C | D | E | F | G | H | I | J | K | L | M | N | O | P | Q | R | T |
| 9 | 10 | 90 | — | — | — | — | — | 80 | — | 100 | — | — | — | — | 90 | 90 | 80 | — | 80 | 80 |
| 10 | 10 | 0 | 80 | 90 | 0 | 0 | 0 | 0 | 95 | 0 | 0 | 0 | 0 | 0 | 0 | 0 | 0 | 0 | 0 | 0 |
| 11 | 0.25 | 0 | 0 | 0 | 0 | 0 | 0 | 80 | 90 | 80 | 0 | 0 | 0 | 0 | 98 | 90 | 90 | 0 | 90 | 0 |
| 13 | 10 | 0 | 0 | 0 | 0 | 0 | 0 | 0 | 0 | 0 | 0 | 0 | 0 | 0 | 0 | 0 | 0 | 0 | 0 | 0 |
| 14 | 10 | — | — | — | — | — | — | 90 | 100 | 90 | — | — | — | — | 98 | 98 | 100 | — | 50 | — |
| 16 | 10 | — | — | — | — | — | — | 80 | 100 | 70 | — | — | — | — | 70 | 98 | 98 | — | 50 | — |
| 17 | 10 | — | — | — | — | — | — | 90 | 100 | 95 | — | — | — | — | 98 | 100 | 98 | — | 90 | — |

We claim:

1. A compound having the formula:

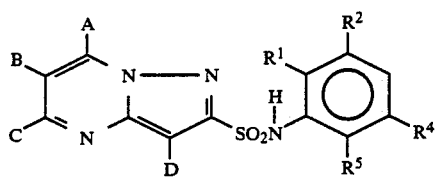

(I)

wherein B represents hydrogen, halogen or $C_1$–$C_4$ alkyl; A, C and D independently represent hydrogen, halogen, $C_1$–$C_4$ alkyl, $C_1$–$C_4$ alkoxy, $C_1$–$C_4$ haloalkyl, $C_1$–$C_4$ haloalkoxy, cyano, hydroxy, $CO_2$ alkyl of 1–3 carbon atoms or A and B or B and C may be bonded together in a cyclic structure —$(CH_2)_n$— where n is 3, 4 or 5; $R^1$ represents F, Cl, Br, I, —$NO_2$, phenyl, —OAr, —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONR^8(R^9)$, —$SO_3R^8$ and —$SO_3CH_2CF_3$; $R^2$ and $R^4$ represent H, F, Cl, Br, $C_1$–$C_4$ alkyl, $COOR^7$ and —$OR^8$; and $R^5$ represents H, $C_1$–$C_4$ alkyl, $C_1$–$C_4$ alkoxy, F, Cl, Br, $NO_2$, $CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, $CONH_2$, $CONHR^8$, —$CONR^8(R^9)$, —$SO_3R^8$, —$SO_3CH_2CF_3$, —$CR^6R^6OR^6$ and —$CR^6R^6SR^6$, wherein $R^6$ represents H, phenyl or $C_1$–$C_4$ alkyl, $R^7$ represents $C_1$–$C_6$ alkyl, $C_3$–$C_6$ alkenyl, $C_3$–$C_6$ alkynyl, phenyl, halo substituted $C_1$–$C_6$ alkyl or halo substituted phenyl and $R^8$ band $R^9$ individually represent $C_1$–$C_4$ alkyl, with the proviso 4. Compound of claim 1 which is 3-cyano-5,7-dimethyl-N-(2,6-difluorophenyl)pyrazolo[1,5-a]pyrimidine-2-sulfonamide.

5. Compound of claim 1 which is 5,7-dimethyl-N-(2,6-difluorophenyl)pyrazolo[1,5-a]pyrimidine-2-sulfonamide.

6. Compound of claim 1 which is 3-carboethoxy-5,7-dimethyl-N-(2,6-difluorophenyl)pyrazolo[1,5-a]pyrimidine-2-sulfonamide.

7. Compound of claim 1 which is 3-chloro-5,7-dimethyl-N-(2,6-difluorophenyl)pyrazolo[1,5-a]pyrimidine-2-sulfonamide.

8. Compound of claim 1 which is 3-carboethyoxy-5,7-dimethyl-N-(2-trifluoromethyl-6-methoxyphenyl)-pyrazolo[1,5-a]pyrimidine-2-sulfonamide.

9. Compound of claim 1 which is 5,7-dimethyl-N-(2-trifluoromethyl-6-methoxyphenyl)pyrazolo[1,5-a]pyrimidine-2-sulfonamide.

10. Compound of claim 1 which is 3-chloro-5,7-dimethyl-N-(2-trifluoromethyl-6-methoxyphenyl)-pyrazolo[1,5-a]pyrimidine-2-sulfonamide.

11. A method of controlling vegetation which comprises applying to the locus of the vegetation a herbicidal compound having the formula:

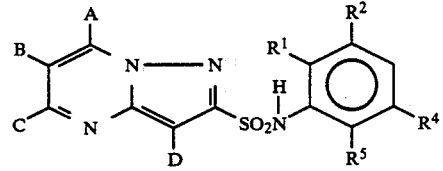

wherein B represents hydrogen, halogen or $C_1$–$C_4$ alkyl; A, C and D independently represent hydrogen, halogen, $C_1$–$C_4$ alkyl, $C_1$–$C_4$ alkoxy, $C_1$–$C_4$ haloalkyl, $C_1$-$C_4$ haloalkoxy, cyano, hydroxy, $CO_2$ alkyl of 1-3 carbon atoms or A and B or B and C may be bonded together in a cyclic structure —$(CH_2)_n$— where n is 3, 4 or 5; $R^1$ represents F, Cl, Br, I, —$NO_2$, phenyl, —OAr, —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONR^8(R^9)$, —$SO_3R^8$ and —$SO_3CH_2CF_3$; $R^2$ and $R^4$ represent H, F, Cl, Br, $C_1$-$C_4$ alkyl, $COOR^7$ and —$OR^8$; and $R^5$ represents H, $C_1$-$C_4$ alkyl, $C_1$-$C_4$ alkoxy, F, Cl, Br, $NO_2$, $CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, $CONH_2$, $CONHR^8$, —$CONR^8(R^9)$, —$SO_3R^8$, —$SO_3CH_2CF_3$, —$CR^6R^6OR^6$ and —$CR^6R^6SR^6$, wherein $R^6$ represents H, phenyl or $C_1$-$C_4$ alkyl, $R^7$ represents $C_1$-$C_6$ alkyl, $C_3$-$C_6$ alkenyl, $C_3$-$C_6$ alkynyl, phenyl, halo substituted $C_1$-$C_6$ alkyl or halo substituted phenyl and $R^8$ and $R^9$ individually represent $C_1$-$C_4$ alkyl, with the proviso that all sulfur containing substituents are in the same oxidation state.

12. A herbicidal composition which comprises an inert agricultural adjuvant or carrier in composition form with a herbicidally effective amount of a compound having the formula:

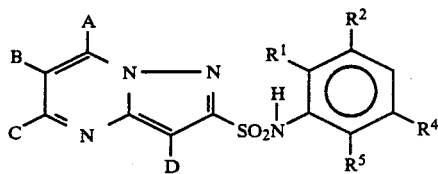

wherein B represents hydrogen, halogen or $C_1$-$C_4$ alkyl; A, C and D independently represent hydrogen, halogen, $C_1$-$C_4$ alkyl, $C_1$-$C_4$ alkoxy, $C_1$-$C_4$ haloalkyl, $C_1$-$C_4$ haloalkoxy, cyano, hydroxy, $CO_2$ alkyl of 1-3 carbon atoms or A and D or B and C may be bonded together in a cyclic structure —$(CH_2)_n$— where n is 3, 4 or 5; $R^1$ represents F, Cl, Br, I —$NO_2$, phenyl, —OAr, —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONR^8(R^9)$, —$SO_3R^8$ and —$SO_3CH_2CF_3$; $R^2$ and $R^4$ represent H, F, Cl, Br, $C_1$-$C_4$ alkyl, $COOR^7$ and —$OR^8$; and $R^5$ represents H, $C_1$-$C_4$ alkyl, $C_1$-$C_4$ alkoxy, F, Cl, Br, $NO_2$, $CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$, —$SO_2R^6$, —CN, —$COOR^7$, $CONH_2$, $CONHR^8$, —$CONR^8(R^9)$, —$SO_3R^8$, —$SO_3CH_2CF_3$, —$CR^6R^6OR^6$ and —$CR^6R^6SR^6$, wherein $R^6$ represents H, phenyl or $C_1$-$C_4$ alkyl, $R^7$ represents $C_1$-$C_6$ alkyl, $C_3$-$C_6$ alkenyl, $C_3$-$C_6$ alkynyl, phenyl, halo substituted $C_1$-$C_6$ alkyl or halo substituted phenyl and $R^8$ and $R^9$ individually represent $C_1$-$C_4$ alkyl, with the proviso that all sulfur containing substituents are in the same oxidation state.

* * * * *